United States Patent
Eakins et al.

(10) Patent No.: US 6,846,303 B2
(45) Date of Patent: Jan. 25, 2005

(54) TAMPER EVIDENT SYRINGE BARREL

(75) Inventors: Michael N. Eakins, East Windsor, NJ (US); Ernest Balestracci, Iselin, NJ (US); Ernst Schramm, North Brunswick, NJ (US); John J. Niedospial Jr., Burlington, NJ (US)

(73) Assignee: Bracco Diagnostics Inc., Princeton, NJ (US)

( * ) Notice: Subject to any disclaimer, the term of this patent is extended or adjusted under 35 U.S.C. 154(b) by 0 days.

(21) Appl. No.: 10/774,852

(22) Filed: Feb. 9, 2004

(65) Prior Publication Data

US 2004/0159564 A1 Aug. 19, 2004

Related U.S. Application Data

(62) Division of application No. 10/265,986, filed on Oct. 7, 2002, which is a division of application No. 09/759,656, filed on Jan. 12, 2001, now Pat. No. 6,485,460.

(51) Int. Cl.[7] .................................. A61M 5/00
(52) U.S. Cl. ................ 604/111; 604/187; 604/192; 604/199; 604/256; 604/263
(58) Field of Search ................. 604/110, 111, 604/181, 187, 197–199, 256, 263

(56) References Cited

U.S. PATENT DOCUMENTS

| | | | |
|---|---|---|---|
| 3,272,322 A | 9/1966 | Ogle | |
| 3,828,775 A * | 8/1974 | Armel | 604/196 |
| 4,106,622 A | 8/1978 | Windischman | |
| 4,187,848 A | 2/1980 | Taylor | |
| 4,671,408 A * | 6/1987 | Raines et al. | 206/365 |
| 4,832,695 A | 5/1989 | Rosenberg et al. | |
| 4,886,497 A | 12/1989 | Scholl | |
| 5,057,088 A | 10/1991 | Narayanan | |
| 5,135,496 A | 8/1992 | Vetter et al. | |
| 5,158,550 A | 10/1992 | Scholl | |
| 5,320,603 A | 6/1994 | Vetter et al. | |
| 5,328,474 A | 7/1994 | Raines | |
| 5,615,772 A | 4/1997 | Naganuma | |
| 5,624,402 A * | 4/1997 | Imbert | 604/111 |
| 5,647,849 A | 7/1997 | Kalin | |
| 5,785,691 A | 7/1998 | Vetter et al. | |
| 5,887,633 A | 3/1999 | Yale et al. | |
| 6,027,482 A | 2/2000 | Imbert | |

(List continued on next page.)

FOREIGN PATENT DOCUMENTS

| | | |
|---|---|---|
| DE | 279468 | 11/1951 |
| EP | 1002551 | 5/2002 |
| GB | 2202747 | 5/1988 |
| WO | WO 96/13289 | 10/1994 |
| WO | WO 94/13338 | 6/1997 |
| WO | WO 00/38615 | 12/1999 |

Primary Examiner—J. Casimer Jacyna
(74) Attorney, Agent, or Firm—Bryan Peckjian; Caragh Noone

(57) ABSTRACT

A prefilled syringe of cartridge barrel having a tamper evident closure. Tamper evidence is provided by: a frangible tip seal which is integral with the tapered tip of the barrel; a frangible tip cap covering the tip, the tip seal and a portion of the distal end of the barrel; and an overwrap covering the frangible tip cap and the distal end of the barrel sealed to the distal end of the barrel by a tamper evident seal. The tapered tip is optionally equipped with a luer collar to receive an external luer connector. Alternatively, the tapered tip can be provided with a bore therethrough which can be closed with an elastomeric plug and the external connector can be a tubing conduit.

9 Claims, 3 Drawing Sheets

U.S. PATENT DOCUMENTS

| | | | |
|---|---|---|---|
| 6,126,640 A | * 10/2000 | Tucker et al. | ................ 604/187 |
| 6,193,688 B1 | 2/2001 | Balestracci et al. | |
| 2001/0003150 A1 | 6/2001 | Imbert | |
| 2002/0069616 A1 | 6/2002 | Odell et al. | |
| 2002/0128612 A1 | 9/2002 | Francavilla et al. | |
| 2002/0143293 A1 | 10/2002 | Andersson et al. | |
| 2003/0032940 A1 | 2/2003 | Doyle | |
| 2003/0040720 A1 | 2/2003 | Steube | |
| 2003/0140477 A1 | 7/2003 | Miller | |
| 2003/0163093 A1 | 8/2003 | Thibault et al. | |

\* cited by examiner

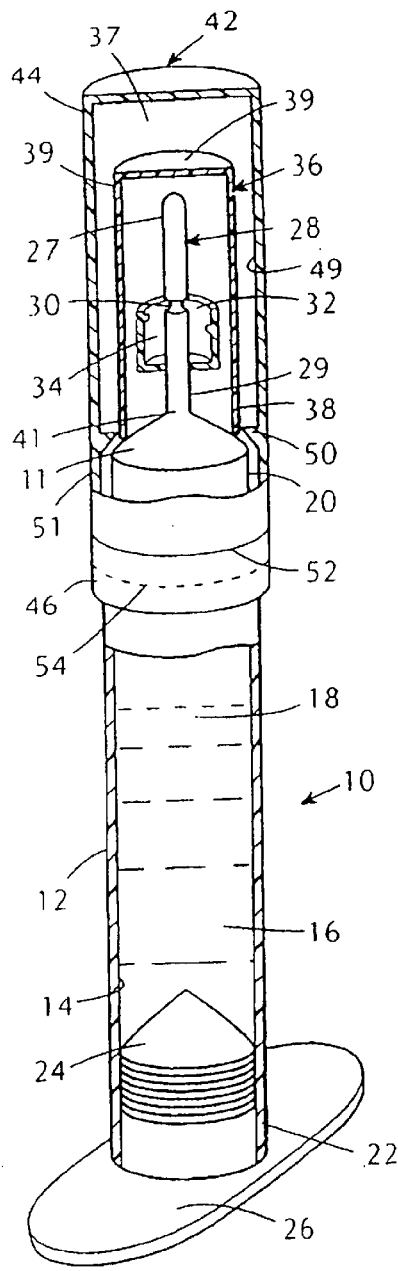
FIG. 1
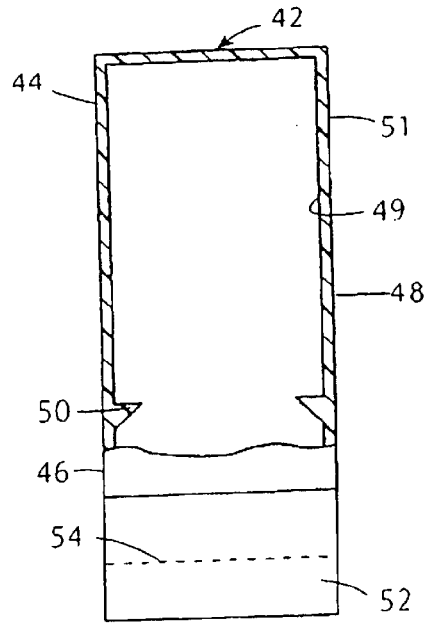
FIG. 2
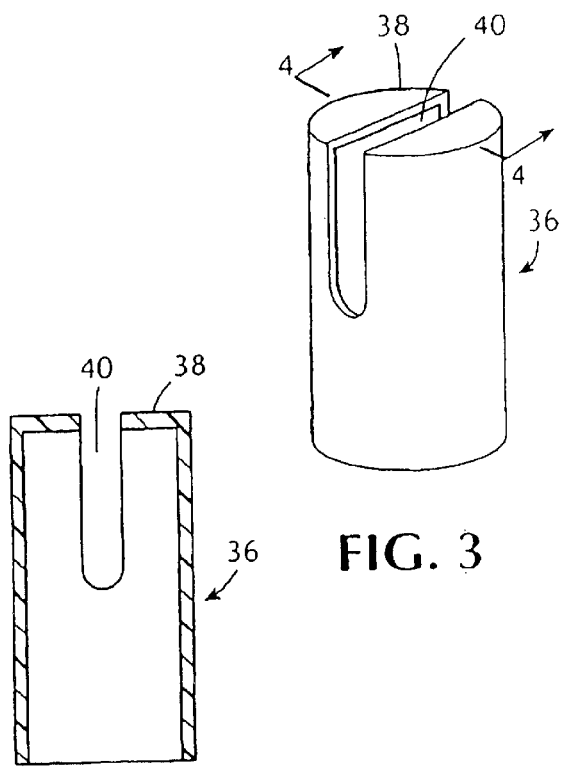
FIG. 3
FIG. 4

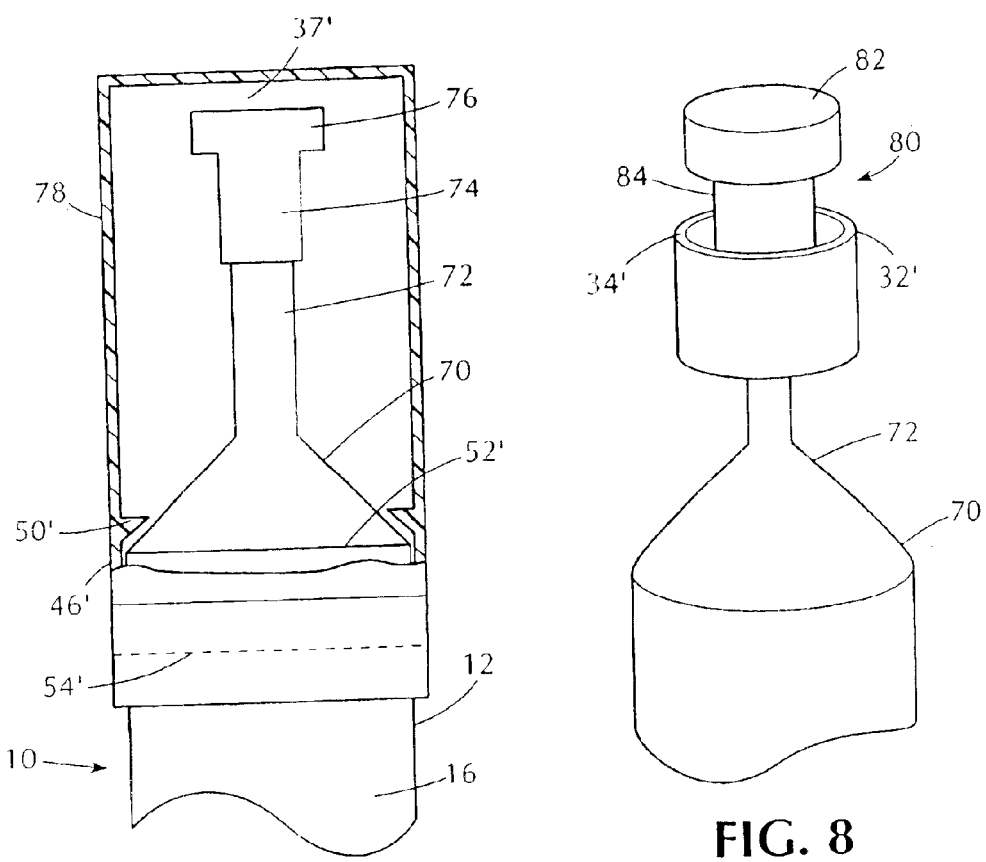
FIG. 7
FIG. 8
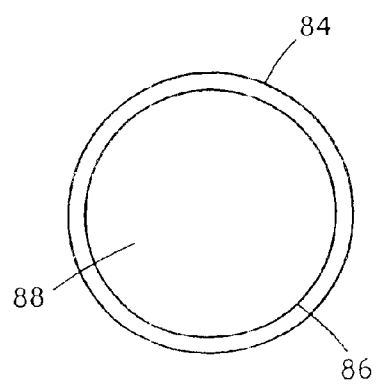
FIG. 9

TAMPER EVIDENT SYRINGE BARREL

This application is a divisional of prior U.S. application Ser. No. 10/265,986, filed Oct. 7, 2002, now U.S. Pat. No. 6,726,652 which is a divisional of U.S. application Ser. No. 09/759,565, filed Jan. 12, 2001, now U.S. Pat. 6,485,460.

FIELD OF THE INVENTION

The present invention relates to a tamper evident cap for a prefilled syringe barrel. More particularly, the invention relates to a tip cap positioned on the distal end of the prefilled syringe barrel and an overwrap enclosing the tip cap and at least a portion of the prefilled syringe barrel.

BACKGROUND OF THE INVENTION

Hypodermic syringes are well-known in the prior art comprising: a cylindrical syringe body having a fluid-receiving chamber therein; a proximal end; and a distal end. The distal end of the syringe body tapers into a tip having a bore therethrough which communicates with the fluid-receiving chamber. The tip is covered with a closure means such as a stopper of a polymeric or elastomeric material, a tip cap or a membrane to prevent leakage and contamination of the fluid medication contained in the syringe barrel. The closure means must be able to be removed with relative ease when the prefilled syringe is to be used.

A plunger is inserted into the open proximal end of the syringe barrel for sliding in fluid-tight engagement with the inside wall of the fluid-receiving chamber. The plunger is equipped with a plunger rod to enable the user to exert pressure on the plunger.

The hypodermic syringe also includes a needle cannula, packaged separately from the syringe barrel, which has a proximal end attachable to the tip of the syringe barrel, and a distal end terminating in a sharp or blunt point. Some hypodermic syringes are equipped with a luer connector to be attached to a corresponding luer collar on the syringe barrel. Additionally, flexible tubing can be placed between the hypodermic syringe and a needle cannula with luer connectors at both ends.

It has been observed that during in-line processing, handling, and sterilizing of the prefilled barrels, some polymeric or elastomeric closures were missing from the tips of the barrels resulting in rejects. Also, during shipment of the finished product and handling by healthcare professionals some untipped barrels were observed which necessitated discarding of batches containing failed samples. For product integrity a corrective measure was indicated to prevent the polymeric or elastomeric closure from becoming dislodged from the tip of the barrel.

More importantly, it has also been recognized that untipped barrels, whether the damage occurred during shipment or handling, attracts the suspicion that the product was tampered with. Such possible tampering is a concern for both the National Regulating Authorities and the manufacturers who are required to insure safety, efficacy and the product integrity.

The prior art has provided various tamper evident closures for syringes.

One reference discloses a tamper evident syringe characterized in that the syringe barrel, the cap, and the plunger rod are covered with a tubular sealing device that is made from a heat-shrinkable film and which has been shrunk under heat so that it adheres closely to the surfaces of those members.

The sealing device comprises a tube and a tear tape. The tube is formed of a transparent heat-shrinkable film. The tear tape is attached by bonding to the inner surface of the tube from one end to the other in the longitudinal direction.

Another reference discloses a hypodermic syringe used with a needle for lyophilized medicament comprising: a syringe body having a piston therein equipped with a tip cap at its distal end; an elastomeric plug having a passage channel closing the neck of the syringe; and a protector cap which encloses the tip cap and the neck portion of the syringe body. The protector cap and tip cap are integral with each other and can be moved axially to open and close the syringe. The protector cap consists of a top portion and a bottom portion, the two parts being held together by a weakened portion. The center of the protector cap is provided with a small hole through which the tip cap can be viewed. In use, the top portion of the protector cap is snapped off at the weakened portion, and the tip cap is taken off and discarded. A needle is then fitted in the passage channel of the elastomeric plug to access the content of the syringe.

Still another reference discloses a syringe cap assembly placed on the distal end of a syringe. The assembly includes: an elastomeric insert having a passage therein; a retaining collar which fits over the elastomeric insert to hold the insert in place; a plug or tip cap is engaged in the insert to block the passage in the insert; and a retaining safety cap fitted over the tip cap. The end wall of the retaining safety cap is formed with a hole in its center and is slightly smaller in diameter than the plug so that the user can ascertain that the plug is properly in its place without opening the assembly.

In use the safety cap is pulled, twisted, and lifted off the assembly. The plug is then lifted off to expose the collar, and a needle assembly is fitted to the collar.

A further reference discloses a prefilled syringe with break-away tip seal which closes the passageway to the content of the syringe. A score means is provided adjacent to the tip for accommodating removal of the sealed tip.

An object of the present invention is to provide a prefilled tamper evident syringe or cartridge barrel which makes apparent the unauthorized use of the medical fluid contained in the barrel of the syringe or cartridge or at least warns healthcare professionals that such unauthorized use may have occurred.

The present invention also addresses the requirement of tailor-making the barrel to provide various degrees of protection against tampering, i.e. certain medical fluids, such as narcotics, lends a grater incentive for tampering than other medical fluids, such as a saline solution. To wit, a barrel containing narcotics should have more than one built-in tamper evidence, although such an approach can equally apply to other medicaments.

Another object of the present invention is to provide tamper evident syringe or cartridge barrels the content of which is easily accessed by the healthcare professionals while their unauthorized use is readily apparent.

A further object of the present invention is to provide a tamper evident syringe or cartridge barrel the content of which can be accessed by luer connections or a tubing conduit so as to avoid the use of "sharps" and thereby preventing needle stick injuries.

SUMMARY OF THE INVENTION

In accordance with the present invention there is provided a prefilled syringe or cartridge barrel equipped with tamper evident closures which indicate unauthorized use of the contents of the syringe of cartridge barrel (hereinafter some-times referred to as "barrel"). The invention consists of four embodiments each of which is designed to be used without sharp or blunt needles so that needle stick injuries as well as the spread of contagious diseases associated with such injuries are prevented.

In one embodiment the present invention comprises:

a) a barrel made of glass or a polymeric material, preferably of transparent polymeric material, containing a medical fluid therein, the proximal end thereof having a slideable elastomeric plunger for expelling the medical fluid from the barrel, and the distal end terminating in a shoulder portion which extends into a tapered tip, said tapered tip having a bore therethrough for fluid communication with the medical fluid in the barrel;

b) a tamper evident closure on the distal end of the barrel comprising:
  1) a tip seal closing the bore and being integral with the tapered tip, said tip seal having a weakened portion for breaking off the tip seal when delivery of the medical fluid is required;
  2) a luer collar around the tapered tip for connection to an external luer connector;
  3) a tip cap covering the distal end of the barrel frangibly connected to the shoulder of the barrel, said tip cap having a slot therein designed to be placed on the tip seal to twist off the tip seal from the tapered tip;
  4) an overwrap having a horizontal top portion, a distal end and a proximal end, covering the tip cap, the shoulder of the barrel and a portion of the barrel; and
  5) a tamper evident seal having a score line therein to seal the proximal end of the overwrap to the distal end of the barrel;

wherein a space or gap is provided between the horizontal top portion of the overwrap and the tip cap to allow grasping the overwrap and remove the same from the barrel.

In another embodiment of the present invention the tip cap further comprises: a centrally positioned cylinder enclosing the tip seal to facilitate breaking off the tip seal from the tapered tip; and an anti-rotation lock between the distal end of the barrel and the tip cap. In this embodiment, the tip cap consists of two portions: an upper portion separated from the lower portion by a breakaway score line. The upper portion is designed to be removed while the lower portion remains on the barrel, the shoulder portion and the tapered tip.

The above-described embodiments provide multiple tamper evidence by having: a tip seal, a tip cap and a overwrap each of which must be removed to reach the content of the barrel. These embodiments are intended to prevent tampering with the barrel containing, for example, narcotics or other medicaments.

In the third embodiment the present invention provides a barrel, having a medical fluid therein, with a tamper evident closure which comprises:

a tamper evident tip cap frangibly connected to the neck of the barrel; an elastomeric plug closing the bore in the tip of the barrel wherein the tip is surrounded by a luer collar; and an overwrap sealed to the barrel by a tamper evident seal. Similarly to the above-described embodiments, a gap is provided between the top portion of the overwrap and the top of the tip cap to allow grasping of the overwrap and removing the overwrap from the barrel.

The fourth embodiment of the present invention is essentially the same as the third embodiment except the luer collar is removed so that no external luer connector is needed to tap the content of the barrel. Instead of an external luer connector a tubing conduit is used one end of which is attached to the open tip of the barrel.

BRIEF DESCRIPTION OF THE DRAWINGS

FIG. 1 is a cross-sectional view of a syringe barrel and plunger equipped with a frangible tip seal, a protector tip cap and overwrap;

FIG. 2 is a plan view of the overwrap;

FIG. 3 is a perspective view of the protector tip cap;

FIG. 4 is a cross-sectional view of the protector tip cap taken along the line 4—4 of FIG. 3;

FIG. 7 is a partial cross-sectional view of another embodiment of the present invention showing a syringe barrel, a protective tip cap with widened upper portion, and an overwrap; and FIG. 8 is a partial perspective view of a syringe barrel, the luer collar and an elastomeric plug covering the tip of the syringe barrel; and FIG. 9 is a bottom plan view of the elastomeric plug.

DETAILED DESCRIPTION OF THE INVENTION

Figure 5:
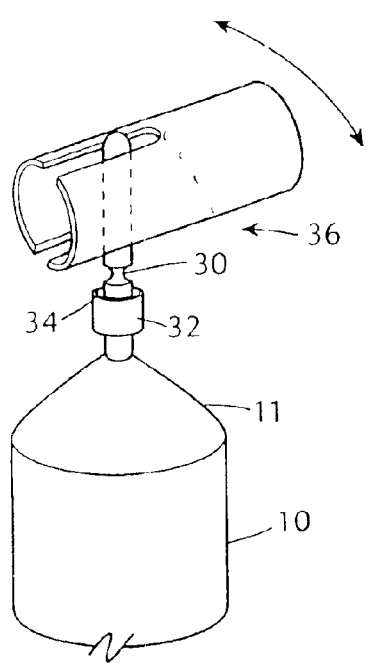
FIG. 5 is a partial perspective view of the syringe barrel and the protector tip cap positioned horizontally on the tip seal during removal of the tip seal at the frangible score line.

In the figures, like numbers denote corresponding elements, while like numbers with prime (') thereon denote like elements;

FIGS. 1–5 show one embodiment of the present invention.

FIG. 1 shows a prefilled syringe or cartridge barrel, generally designated by the numeral 10, made of glass or a polymeric material, having an outside wall 12, an inside wall 14 defining a cylindrical chamber 16 which contains an injectable sterile fluid therein 18, a distal end 20, a proximal end 22, a plunger 24 slideably positioned in the barrel, and a flange 26 on the proximal end.

At its distal end the barrel terminates in a tapered sealed tip generally designated by the numeral 28 and comprises a distal end 27 and a proximal end 29. The sealed tip has a breakaway score means or weak portion 30 adjacent to the tip seal portion for breaking the tip seal portion off the distal end of the barrel to form an opening which, along with a bore in the tip seal, forms a passageway through which the injectable sterile fluid may be expelled by advancing the plunger from the proximal end towards the distal end of the barrel. The tip seal prevents the injectable fluid, such as therapeutic and diagnostic substances to be expelled prior to it being broken off at the score means or weakened portion as well as preventing the entry of contaminants into the sterile injectable fluid contained in the barrel.

The tip seal is surrounded by a cylindrical luer collar 32 having internal spiral threads 34 therein for attaching a corresponding IV catheter thereto having external spiral threads thereon. When the tip seal is detached, an outlet is created which allows fluid communication between the content of the barrel and the IV catheter.

Surrounding the tip seal 28 and the cylindrical luer collar 32 is a tip cap, generally designated by the numeral 36, which at its proximal end 38 is sealed to proximal end 29 of the tip seal 28 with a thermoplastic or other suitable material. The seal so formed is frangible so that the tip cap can be easily separated from the tapered tip seal by breaking off the tip cap.

As shown in FIGS. 1, 3, 4 and 5, tip cap 36 is provided with a slot 40 at the proximal end 38 thereof having a width sufficient to accommodate the tapered tip seal after the tip cap is separated from the tapered tip seal. The steps to provide access to the sterile injectable fluid includes: breaking off the tip cap 36 from the tip seal 27 at the proximal end 38 of the tip cap 36; placing the tip cap onto the tip seal by putting the tip cap onto the tip seal so that the tip seal is positioned in the slot of the tip cap; and twisting the tip cap in a horizontal direction thereby separating the tip cap from the tip seal at the frangible area 41.

Referring to FIGS. 1 and 2, the distal end 20 of syringe or cartridge barrel 10 including tip seal 28 and luer collar 32 enclosed within tip cap 36, is further enclosed by an overwrap, generally designated by the numeral 42. The overwrap having a distal end 44, a proximal end 46 and a side wall 48 of cylindrical configuration closed at its distal end and open at its proximal end.

The overwrap is made of a polymeric sheet, preferably of two or more layers superimposed on each other and sealed together at their peripheries to form a cylindrically shaped body. The inside layer 49 is formed with an overwrap ridge 50 projecting towards the barrel. The outside layer 51 of the overwrap is continuous forming the top and side portions of the overwrap. A tamper evident seal 52 closes the proximal end of the overwrap to the outside wall 12 of the barrel 10. A frangible score line 54 running horizontally in the tamper evident seal renders the overwrap removable when delivery of the sterile injectable fluid is desired from the syringe or cartridge barrel.

In covering a portion of the syringe or cartridge barrel, the tip cap and tip seal, the overwrap is slid towards the proximal end of the barrel until overwrap ridge 50 reaches the top tapered portion 11 of the barrel 10. The overwrap ridge anchors the overwrap to the tapered portion of the barrel. For glass barrels the anchoring is accomplished by providing a groove in the tapered top portion of the barrel into which the plastic ridge snaps. For plastic barrels the anchoring is accomplished by forming a ridge in the plastic tapered portion of the barrel. In both cases, when removal of the overwrap is desired, the overwrap is dislodged from the groove or ridge of the barrel by pulling the overwrap toward the distal end of the barrel. In reference to FIG. 1, it is to be noted that a space 37 is provided between the inside layer 49 of the overwrap 42 and top portion of tip cap in order to allow gripping the overwrap 42 when removal of same is desired.

As can be seen, this embodiment of the present invention provides a prefilled syringe or cartridge barrel for injection of a sterile medical fluid where the injection can be accomplished by hand, or a power injector such as disclosed, for example, by U.S. Pat. No. 5,322,511. The tip seal integrally formed with the barrel prevents entry of contaminants from contacting the sterile medical fluid in the barrel prior to use or leakage of medical fluid from the barrel. The tip seal also provides a measure of security that the content of the barrel has not be tampered with. However, the present invention also provides more apparent signs of tampering by the use of a tip cap and an overwrap as components of the present invention. In order to get to the content of the barrel: first, the overwrap must be removed leaving the lower or proximal portion thereof on the barrel and showing at the score line that the overwrap has been removed; second, the tip cap must be removed which also leaves a score line on the proximal end of the tip seal; and third, the top portion of the tip seal must be broken off in order to open the fluid channel to the content of the barrel.

Figure 6:
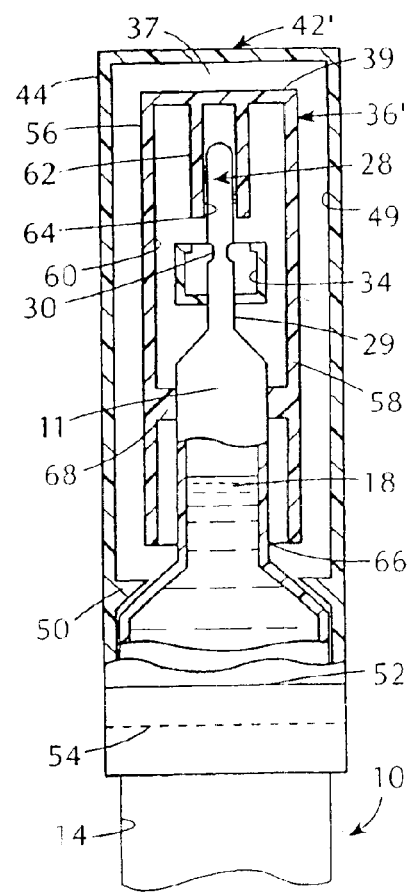
FIG. 6 is a partial cross-sectional view of another embodiment of the present invention showing the distal end of a syringe barrel, a frangible tip seal, a protective tip cap having two portions, and an overwrap.

Another embodiment of the present invention is shown in partial cross-sectional view in FIG. 6 wherein like numerals denote corresponding elements shown in FIGS. 1–5 except the tip cap having a prime (') thereon. Additional parts not shown in FIGS. 1–5 are denoted by additional numerals.

Tip cap 36' comprises two parts: an upper part 56 and a lower part 58. The upper and lower parts are separated form each other by a breakaway score line 60. The upper part is designed to be broken off while the lower part remains on the syringe or cartridge barrel 10. The upper part contains a centrally positioned cylinder 62 extending from the top wall 39 of the tip cap and terminates at the score line 60. The inside wall 64 of centrally positioned cylinder 62 runs parallel to tip seal 28 and is in contact therewith. Cylinder 62 serves to hold tip seal 28 and helps to remove the tip seal at the weak portion 30 thereof Lower part 58 of tip cap 36' extend from breakaway score line 60 to and including the upper portion of the syringe barrel. The distal end 66 of lower part 58 is molded to the syringe barrel by a method known in the art. Additionally, the lower part 58 of tip cap 36' is provided with an anti-rotation lock 68, made of a polymeric material which holds the syringe barrel and the lower part of the tip cap together and prevents rotation of the lower part of the tip cap when the upper part of the tip cap is being removed. The anti-rotation lock may be affixed between the syringe barrel and the tip cap by an adhesive or, preferably, a thermoplastic polymer. Most preferably, both the tip cap and the anti-rotation lock are made of thermoplastic materials.

When it is desired to establish fluid communication between the syringe barrel and an external access means, such as an IV set having a luer lock corresponding with the luer collar shown in FIG. 6, the following steps must be accomplished: removing the overwrap which encloses a portion of the syringe barrel thereby disclosing the frangible score line 54; removing the upper part of the tip cap which discloses breakaway score line 60; and removing tip seal 28 by breaking off the same at weak portion 30. At each step, if the device has been tampered with, the healthcare practitioner would be warned of the likelihood of tampering.

FIG. 7 shows, in a partial cross-sectional view, a syringe barrel having a widened tip cap covering the distal end of the syringe barrel and an overwrap covering the tip cap and the top portion of the syringe barrel. This embodiment of the present invention is directed to a syringe barrel of simple, inexpensive construction which has a built-in feature that warns the healthcare professional that the syringe might have been tampered with.

The syringe barrel 10 comprises: a cylindrical chamber 16 which contains a medical fluid therein; a tapered shoulder 70 extending into neck portion 72 towards the distal end of the syringe. Neck portion 72 at that distal end thereof is covered with a tip cap 74 which widens into a top portion 76. The widened top portion facilitates removal of the tip cap. Overwrap 78 encloses a portion of the syringe barrel, the shoulder 70 of the syringe barrel and the tip cap 74 with its widened top portion 76. The overwrap comprises at least two layers of polymeric film: outside layer and inside layer. The inside layer is provided with ridge 50' projecting inwardly towards the shoulder 70 of syringe barrel 10. Space 37' is provided between the widened portion of tip cap 76 and the inside layer of the overwrap. Tamper evident seal 52' having frangible score line 54' therein seals the overwrap to the outside wall 12 of barrel 10. Tip cap 74 is sealed to neck 72 by an adhesive or a thermoplastic means.

FIG. 8 is a fragmentary cross-sectional view of the distal end of the syringe barrel, luer collar, and elastomeric plug 80. The luer collar and the elastomeric plug are hidden under tip cap 74 in FIG. 7. The distal end of the barrel, in this embodiment of the present invention, terminates in a tapered tip having a bore therethrough. The tapered tip is surrounded by cylindrical luer collar 32' having internal spiral threads therein. The luer collar is designed to receive an external access means, such as an IV set, with a corresponding luer connection. As seen in FIGS. 8 and 9, elastomeric plug 80 is of cylindrical configuration having a distal and a proximal end comprising: a closed portion 82 at the distal end, an open portion at the proximal end, outside wall 84 and inside wall 86 connecting the top and bottom portions. The inside wall defines a cylindrical chamber 88. The elastomeric plug is positioned within the wall of the luer collar so that the cylindrical chamber covers the open tip of the syringe barrel. When delivery of the medical fluid is desired the elastomeric plug is removed.

The tamper evident syringe barrel in this embodiment of the present invention is also provided without the luer collar 32'. When delivery of the medical fluid is desired the elastomeric plug 80 is removed and one end of a tubing conduit is attached to the open tip of the barrel. The other end of the tubing conduit is equipped with a syringe through which the medical fluid is administered to the patient.

The method of accessing the medical fluid contained in the syringe barrel includes the steps of:

removing the tamper evident seal at the score line from the syringe barrel;

removing the overwrap by holding or pulling on the top portion of the overwrap;

removing the tip cap by holding the widened portion thereof and turning the same in either direction;

removing the elastomeric plug from the top of the syringe barrel;

connecting an external access means to the open tip of the barrel; and advancing the plunger in the barrel in the distal direction.

Materials of Construction

The syringe or cartridge barrel is made of glass or known polymeric materials, preferably a transparent polymeric material. The barrel can be coated with a UV barrier coating.

The UV barrier coating is a clear flexible film made of polymers having UV absorbing (scavenging) or oxygen absorbing (scavenging) properties so that the content of the container is not affected by environmental conditions. These polymers include in the form of a film alloys, blends, extrusions, laminations, surface modified and impregnated films or combinations thereof of the following polymeric materials which are capable to withstand autoclave or high-temperature sterilization and which contain UV absorbing or oxygen scavenging agent or into which such agents are incorporated by processes known to those skilled in the art:

copolyester elastomers,
ethylene methacrylate,
ethylene vinyl acetate,
ethylene vinyl alcohol,
low density polyethylene,
nylon/polypropylene,
polyester,
polyolefin,
polypropylene,
polyethylene and
polyvinylchloride.

Blocking agents/UV stabilizers which may be included in the films include:

N-(2-Aminoethyl)-3-aminopropylmethyldimethoxy silane; 3-Aminopropylmethyl-diethoxy silane; Amyitrichlorosilane;

Bis (hydroxyethyl) aminopropyltriethoxy silane; Bis-(N-methylbenzanide) ethoxymethyl silane; Bis (trimethylsilyl)acetamide;

3-Chloropropyltriethoxysilane;

Di-t-butoxydiacetoxysilane;

Ethyltriacetoxysilane;

(3-Glycidoxypropyl)-methyldiethoxy silane;

Isobutyltrimethoxysilane; Isocyanatopropyltriethoxysilane;

3-Mercaptopropylmethyldimethoxysilane; Mercaptopropyltrimethoxysilane;

N-methylaminopropyltrimethoxysilane; Methyltriacetoxysilane; Methyltriethoxysilane; Methyl trimethoxysilane;

Octyltriethoxysilane;

2-Phenylethyltrichlorosilane; Phenyltriethoxysilane; n-Propyltrimethoxysilane 3-(N-Styrylmethyl-2-aminoethylamino) propyltrimethoxy silane hydrochlorid;

2-(3'-t-butyl-2'-hydroxy-5'-methylphenyl)-5-chlorobenzotriazole; and

Bis (1,2,2,6,6,-pentamthyl-4-piperidinyl)(3,5-di-t-butyl-4-hydroxybenzyl)butyl propanedioate and ethyl 2-cyano-3,3-diphenylacrylate.

The protective cap is made of a polymeric material including: polyolefins such as polyethylene and polypropylene; polystyrene, polycarbonate, polymethylpentene, cyclic olefin co-polymers, acrylic polymers and methacrylic polymers.

The elastomeric plug is preferably of soft rubber.

The overwrap used in the present invention can be a monolayer film, however, multilayer films are preferred. The sheets are made of known polymeric materials having properties which make them suitable for use under conditions of steam and gamma rays sterilization. Such properties include gloss, strength, flexibility and chemical inertness. Preferably, the sheets are transparent or at least translucent enabling visual inspection of the contents at all times prior to and during delivery of the content from the barrel to the patient. The sheets may be made, for example, from polyvinylidine chloride between two polyethylene or polyvinyl acetate layers. Further layers may be added to the face or back of the sheet, if desired, such as polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$ days at 38° C., 100% RH); and an oxygen barrier of 650 (cc/m$^2$/day at 23° C., 0% RH, bar. CRYO-VAC® sterlizable medical films (W.R. Grace and Co.) are especially suitable to construct the sheets used in the present invention. The films comprise a polyethylene layer between polyester outer layers sealed together by a modified propylene co-polymer. Typical properties of the film include: a thickness of about 190 micron; a tensile strength of about 250 kg/cm$^2$; a moisture vapor transmission rate of 5 (g/m$^2$/day at 38° C., 100% RH); and an oxygen barrier of about 1500 (cc/m$^2$/day at 23° C., 0% RH, bar).

Other preferred polymeric films or sheets for constructing the flexible overwrap of the present invention include: copolyester ether monolayer films, such as polycyclohexanedimethylcyclohexane dicarboxylate elastomer made by Eastman Chemical Co.

PARTS LIST

Syringe or cartridge barrel, generally designated 10
Top tapered portion of barrel 11
Outside wall of barrel 12
Inside wall of barrel 14
Cylindrical chamber in barrel 16
Injectable sterile fluid in barrel 18
Distal end of barrel 20
Proximal end of barrel 22
Plunger in barrel 24
Flange on barrel 26
Tip seal, generally designated 27
Distal end of tip seal 28
Proximal end of tip seal 29
Weak portion on tip seal 30
Cylindrical luer collar on tip seal 32, 32'
Internal spiral threads on cylindrical luer collar 34, 34'
Tip cap, generally designated 36, 36'
Space between top portion of tip cap and inside layer of overwrap 37, 37'
Proximal end of tip cap 38
Distal end of tip cap 39
Slot in tip cap 40
Frangible area of tip cap sealed to tip seal 41
Overwrap, generally designated 42, 42'
Distal end of overwrap 44
Proximal end of overwrap 46
Side wall of overwrap 48
Inside layer of overwrap 49
Overwrap ridge 50, 50'
Outside layer of overwrap 51
Tamper evident seal 52, 52'
Frangible score line on tamper evident seal 54, 54'
Upper part of tip cap 56
Lower part of tip cap 58
Breakaway score line between upper part and lower part of tip cap 60
Centrally positioned cylinder in the upper part of tip cap 62
Inside wall of cylinder 64
Distal end of lower part of tip cap 66
Anti-rotation lock 68
Shoulder portion of syringe barrel 70
Neck portion of syringe barrel 72
Tip cap 74
Widened portion of tip cap 76
Overwrap 78
Elastomeric plug, generally designated 80
Top portion of elastomeric plug 82
Outside wall of elastomeric plug 84
Inside wall of elastomeric plug 86
Cylindrical chamber in elastomeric plug 88

Having described the invention, it will be apparent to those skilled in the art that various changes and modifications may be made thereto. It is intended to include such changes and modification limited only by the scope of the appended claims.

What is claimed is:

1. A prefilled tamper evident syringe barrel comprising:
   a) a syringe barrel of glass or polymeric material having an inner surface defining a chamber having a medical fluid therein, said syringe barrel comprising:
      a distal end terminating in a shoulder portion and a tapered tip; and
      a proximal end containing a plunger slideably positioned in the syringe barrel;
      wherein said tapered tip comprises: a distal end and a proximal end, said distal end being closed by a tip seal; wherein said tapered tip has a breakaway score means adjacent to said distal end for facilitating removal of said tip seal thereby forming a passageway through which said medical fluid can be expelled from the syringe barrel;
   b) a tamper evident tip cap of cylindrical configuration having a closed distal end and an open proximal end comprising: (1) an upper part and (2) a lower part, said upper part and said lower part connected to each other by a breakaway score line; a centrally positioned cylinder in said upper part extending from said closed distal end towards said proximal end of the tamper evident tip cap terminating in said breakaway score line and serving to securely hold said tip seal; said lower part of said tamper evident tip cap being sealed at its proximal end to the distal end of said syringe barrel, said lower part comprising an anti-rotation lock connecting said lower part to said syringe barrel;
   c) an overwrap of cylindrical configuration having a closed distal end and an open proximal end, said overwrap being provided with a ridge adjacent to the proximal end thereof projecting towards the shoulder of said syringe barrel and resting thereon; wherein said overwrap encloses a portion of said syringe barrel, said shoulder portion and said tip cap; and
   d) a tamper evident seal of cylindrical configuration having an open distal end and an open proximal end, provided with a fragible score line, which seals said proximal end of said overwrap to the said syringe barrel.

2. The prefilled tamper evident syringe barrel of claim 1 wherein said tip seal is surrounded by a luer collar position adjacent to said breakaway score means adapted to receive an external luer connector.

3. The prefilled tamper evident syringe barrel of claim 1 wherein said overwrap is a monolayer film.

4. The prefilled tamper evident syringe barrel of claim 3 wherein said monolayer film is polycyclohexanedimethyl-cyclohexane dicarboxylate.

5. The prefilled tamper evident syringe barrel of claim 1 wherein said overwrap is a polyvinylchloride layer between two polyethylene layers.

6. The prefilled tamper evident syringe barrel of claim 1 wherein said overwrap is a polyvinylchioride layer between two polyvinyl acetate layers.

7. The prefilled tamper evident syringe barrel of claim 1 wherein said overwrap is a polyethylene layer between polyester outer layers sealed together by a propylene copolymer.

8. The prefilled tamper evident syringe barrel of claim 1 wherein said tamper evident tip cap is made of a polymeric material selected from the group consisting of polyethylene, polypropylene, polystyrene, polycarbonate, polymethylpentene, cyclic olefin polymers, acrylic polymers and methacrylic polymers.

9. The prefilled tamper evident syringe barrel of claim 1 wherein said tamper evident syringe barrel is coated with a UV barrier coating.

* * * * *